United States Patent
Huttner et al.

(12)

(10) Patent No.: US 6,706,023 B1
(45) Date of Patent: Mar. 16, 2004

(54) DEVICE FOR IRRIGATION OF A BLIND ORIFICE

(75) Inventors: James J. Huttner, Sylvania, OH (US); David I. Kinsel, Sylvania, OH (US); Josh A. Noble, Oak Harbor, OH (US)

(73) Assignee: Bionix Development Corporation, Toledo, OH (US)

( * ) Notice: Subject to any disclaimer, the term of this patent is extended or adjusted under 35 U.S.C. 154(b) by 0 days.

(21) Appl. No.: 09/454,138

(22) Filed: Dec. 3, 1999

(51) Int. Cl.[7] .................................................. A61M 5/00
(52) U.S. Cl. ......................................................... 604/264
(58) Field of Search ................................ 604/27, 35, 39, 604/43–45, 264, 272, 523, 534, 535

(56) References Cited

U.S. PATENT DOCUMENTS

| | | |
|---|---|---|
| 3,651,808 A | 3/1972 | White |
| 4,036,235 A | 7/1977 | Hathaway |
| 4,206,756 A | 6/1980 | Grossan |
| 4,244,377 A | 1/1981 | Grams |
| 4,548,597 A * | 10/1985 | Nelson ........................ 604/43 |
| 4,904,238 A * | 2/1990 | Williams ..................... 604/264 |
| 5,176,654 A | 1/1993 | Schreiber |
| D340,112 S | 10/1993 | Zeman |
| 5,309,899 A | 5/1994 | Ginsberg |
| 5,364,343 A | 11/1994 | Apolet et al. |
| 5,395,357 A | 3/1995 | Weigel |
| 5,662,605 A | 9/1997 | Hurwitz |
| 5,674,196 A | 10/1997 | Donaldson et al. |
| 5,685,851 A | 11/1997 | Murphy et al. |
| 5,833,675 A | 11/1998 | Garcia |
| 5,888,199 A | 3/1999 | Karell et al. |
| 5,916,150 A | 6/1999 | Sillman |

OTHER PUBLICATIONS

Ethicare™ Products Home Use Products and Professional Office Products order from, by Ethicare Products of Fort Lauderdale, Florida, order form prices effective Sep. 1, 1999, otherwise no publication date on order form.

* cited by examiner

Primary Examiner—Brian L. Casler
Assistant Examiner—Michael M Thompson
(74) Attorney, Agent, or Firm—Emch, Schaffer, Schaub & Porcello Co., L.P.A.

(57) ABSTRACT

The present invention relates to an irrigation device for use in an orifice. The device has a tubular member having a distal end and a proximal end and at least one bore axially extending from the proximal end to the distal end. The bore terminates at a plurality of orifices which extend at an angle from the bore. As an additional feature, the tubular member can define an internal baffle which extends in a direction from the distal end to the proximal end of the tubular member. The internal baffle aids in deflecting a stream of pressurized fluid out the orifices of the tubular member. A flared member is coaxially positioned with respect to the tubular member. The flared member defines a tip in close proximity to the distal end of the tubular member and a base which is in a spaced apart relationship from the tip. The flared member defines a plurality of flared sides extending from the tip to the base. As the flared sides extend from the tip to the base, the flared sides increase in circumference. The flared member also defines at least one passageway which defines at least one open channel adjacent the tip of the flared member and at least one enclosed channel adjacent the base of the flared member. The enclosed channel is defined by the flared sides and the base of the flared member.

30 Claims, 8 Drawing Sheets

DEVICE FOR IRRIGATION OF A BLIND ORIFICE

TECHNICAL FIELD

This invention relates to an irrigation device for use with a pressurized irrigating fluid to remove materials from an orifice. The device comprises a tubular member having a plurality of orifices that direct the irrigating fluid away from a central axis of the device and a flared member having a plurality of exit passages for evacuation of the fluid and debris without the build-up of excessive pressure which could damage the delicate anatomy of the blind orifice.

BACKGROUND OF THE INVENTION

Irrigation has often been used by physicians to flush debris from blind orifices such as the ear canal. Removal of obstructing cerumen, or ear wax, is important to properly view the tympanic membrane, a sensitive and fragile piece of anatomy. Removal of cerumen is a necessary requirement to properly diagnose possible infection. Other means of removal are also employed to remove the cerumen, such as an ear curette. These removal means, however, are dangerous in unskilled hands as unintentional puncture of the tympanic membrane or laceration of the ear canal is possible.

Irrigation and flushing of the ear canal to remove cerumen can avoid these risks to a certain degree. Prior art devices intended for this function abound, but lack elements of the present invention, making them less than ideal. Devices advancing the state of the art beyond simple syringes and bulbs, such as those described by Grossan (U.S. Pat. No. 4,206,756), Ginsberg (U.S. Pat. No. 5,309,899), Apolet et al. (U.S. Pat. No. 5,364,343), Murphy et al. (U.S. Pat. No. 5,685,851, and Garcia (U.S. Pat. No. 5,833,675) do not contain the combination of novel features described by this invention.

SUMMARY OF THE INVENTION

The present invention relates to an irrigation device for use in an orifice. The irrigation device has a tubular member having a distal end and a proximal end and at least one bore axially extending from the proximal end to the distal end. The axially extending bore terminates at a plurality of orifices which extend at an angle from the bore. As an additional feature, the tubular member can define an internal baffle which extends from the distal end toward the proximal end of the tubular member. The internal baffle aids in deflecting a stream of pressurized fluid out the orifices of the tubular member. A flared member is coaxially positioned with respect to the tubular member. The flared member defines a tip in close proximity to the distal end of the tubular member and a base which is in a spaced apart relationship from the tip. The flared member defines a plurality of flared sides extending from the tip to the base. As the flared sides extend from the tip to the base, the flared sides increase in circumference. The flared member also defines at least one passageway which defines at least one open channel adjacent the tip of the flared member and at least one enclosed channel adjacent the base of the flared member. The enclosed channel is defined by the sides and the base of the flared member.

The present invention relates to an irrigation device for use with a pressurized irrigating fluid. The present invention is especially useful in irrigating blind orifices and is of particular use in medical fields. The present invention is particularly well suited for use in irrigating ear canals, nasal passageways and vaginas. For ease of explanation, the present invention will be described in detail for use in irrigating an ear canal. However, it should be understood, that the device can be made in various sizes for use in both medical and other commercial applications.

DESCRIPTION OF THE PREFERRED EMBODIMENT

Figure 1:
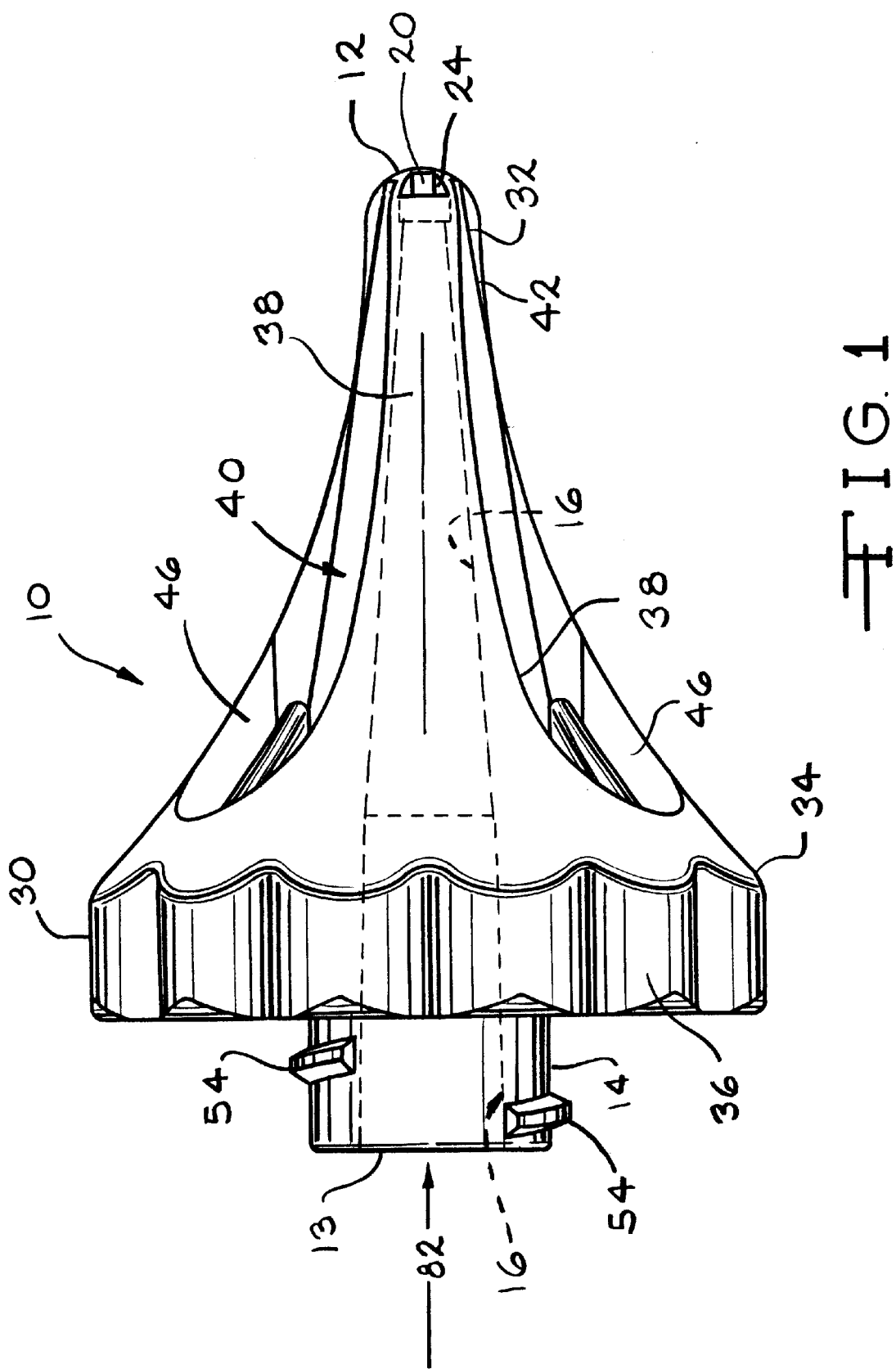
FIG. 1 is a side elevation view, partially in phantom, of an irrigation device.
Figure 2A:
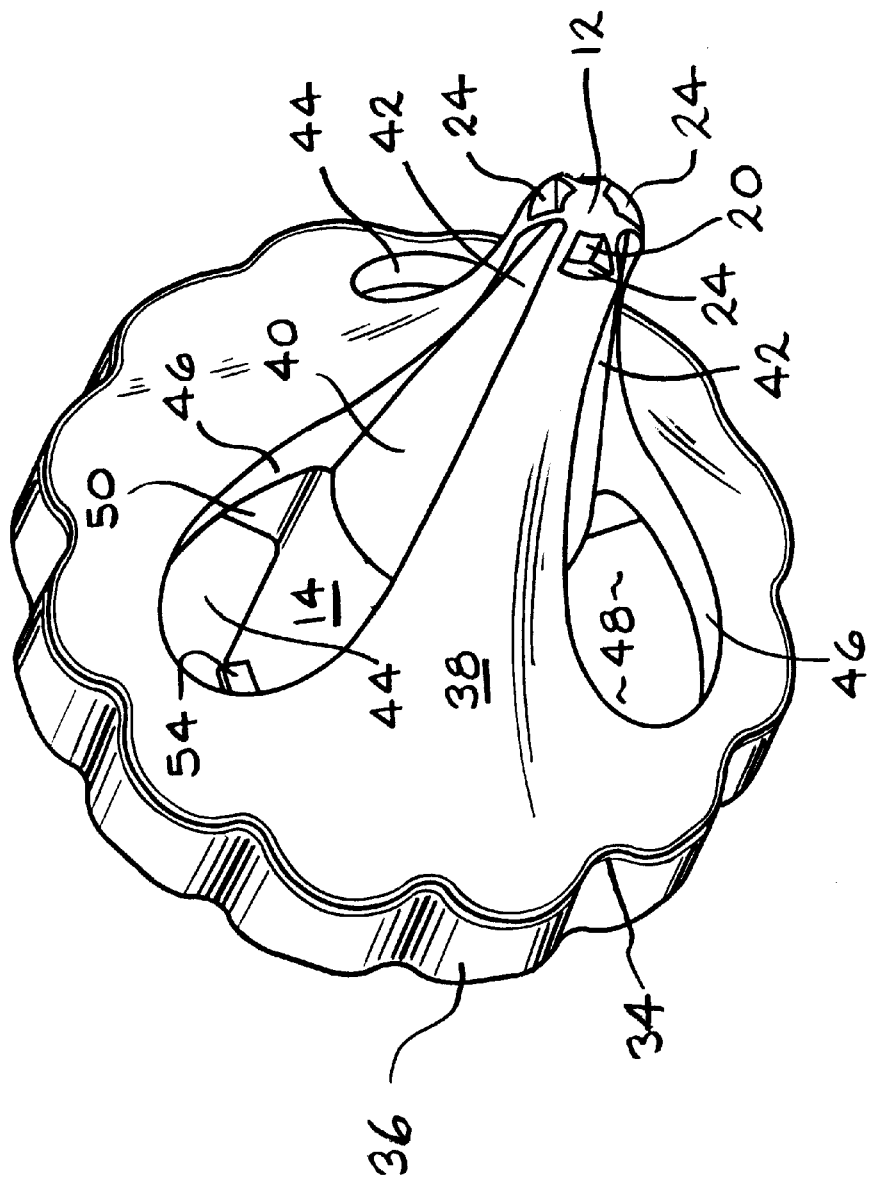
FIG. 2A is a front perspective view of an irrigation device.
Figure 4:
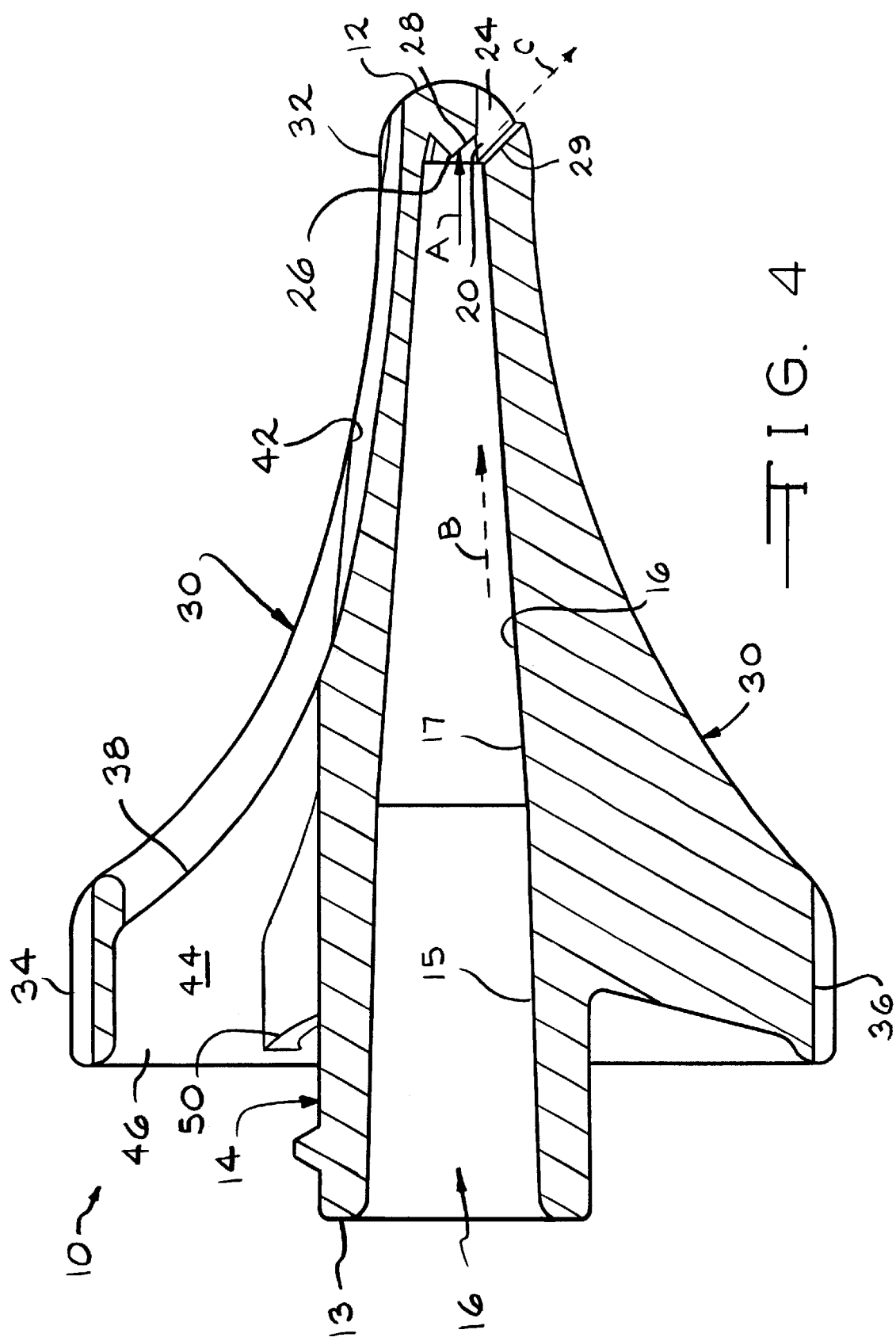
FIG. 4 is a cross-sectional view of an irrigation device.

Referring to FIGS. 1, 2 and 4, an irrigation device 10 is generally shown. The irrigation device 10 has a distal end 12 and a proximal end 13. The irrigation device 10 comprises a tubular member 14 which defines an opening or bore 16 axially extending from the proximal end 13 and terminating at the distal end 12. The bore 16 has a tapered shape such that the internal diameter of the bore 16 adjacent the proximal end 13 is greater than the internal diameter of the bore 16 adjacent the distal end 12. As an additional feature, the bore 16 can have a variable taper as shown in FIG. 4. The bore 16 can have a first internal tapered surface which has a decreasing circumference as the bore 16 extends toward the distal end 12. The bore 16 can also have a second internal tapered surface 17 which also has a decreasing circumference as the bore 16 extends toward the distal end 12. As shown in FIG. 4, the first tapered surface 15 slopes toward the distal end 12 at an angle α, as defined by a line C through the center of the bore 16, that is different from the shape angle β, as defined by the line C, of the second tapered surface 17. It is to be understood that it is within the contemplated scope of the present invention that the internal surface of the bore 16 can have other configurations such as multiple tapered surfaces, axially extending grooves and the like.

The surface of the bore 16 acts to direct fluid in the bore toward at least one, and preferably a plurality of, orifices 20 which extend from the axially extending bore 16. In one example, each orifice 20 is positioned with radial symmetry around a central axis extending through the bore 16. Each orifice 20 terminates at and communicates with a recessed cavity 24 that extends though the distal end 12 of the tubular member 14 and into communication with the bore 16.

It is within the contemplated scope of the present invention that the device 10 can have a plurality of orifices 20 extending through the distal end 12, preferably from about 2 to about 10 orifices. It is further to be understood that the orifices can have a predetermined geometric cross-sectional configuration including but not limited to, round, rectangular, triangular, and elliptical and the like. It should be understood that other geometric cross-sectional configurations are within the contemplated scope of the present invention.

The orifices 20 are large enough to allow the fluid to exit the bore at a preferred angle. The pressurized irrigating fluid exits through the orifices 20 and emerges into the recessed cavities 24 in a direction that is at an angle of about 75°–90° or less to the central axis of the bore 16.

The distal end 12 of the tubular member 14 defines an internal baffle or internal fluid directional member 26 having at least one side wall 28. The internal baffle 26 extends in an axial direction toward the proximal end 13 of the tubular member 14. A stream of pressurized fluid flowing through the bore 16 contacts the side wall 28 of the internal baffle 26 and is deflected toward the orifices 20. As the fluid is being deflected from the side walls 28 of the internal baffle 26, the fluid is further directed by at least one side wall 29 of the recessed cavity 24. The pressurized fluid is directed against the side wall 29 of the recessed cavity 24 and from there, toward the wall of the ear canal rather than directly at the tympanic membrane.

In certain applications, it is desired that the side wall 28 of the internal baffle 26 be substantially parallel to the side wall 29 of the recessed cavity 24. The parallel relationship between the side wall 28 and the side wall 29 further directs the fluid in the direction created by the baffle 26. In a preferred application, side walls 28 of the internal baffle 26 have an included angle of between about 60° to about 120° and in certain embodiments, about 30° to about 45°. The baffle 26 can have a conical shape, as shown in FIG. 4. However, it is also within the contemplated scope of the present invention that the internal baffle 26 can have any suitable geometric configuration, such as spherical, tetrahedral and the like, that will direct or divert a stream of pressurized fluid to the orifices 20. It is also within the contemplated scope of the present invention that the internal baffle can have other geometric configurations.

Figure 5:
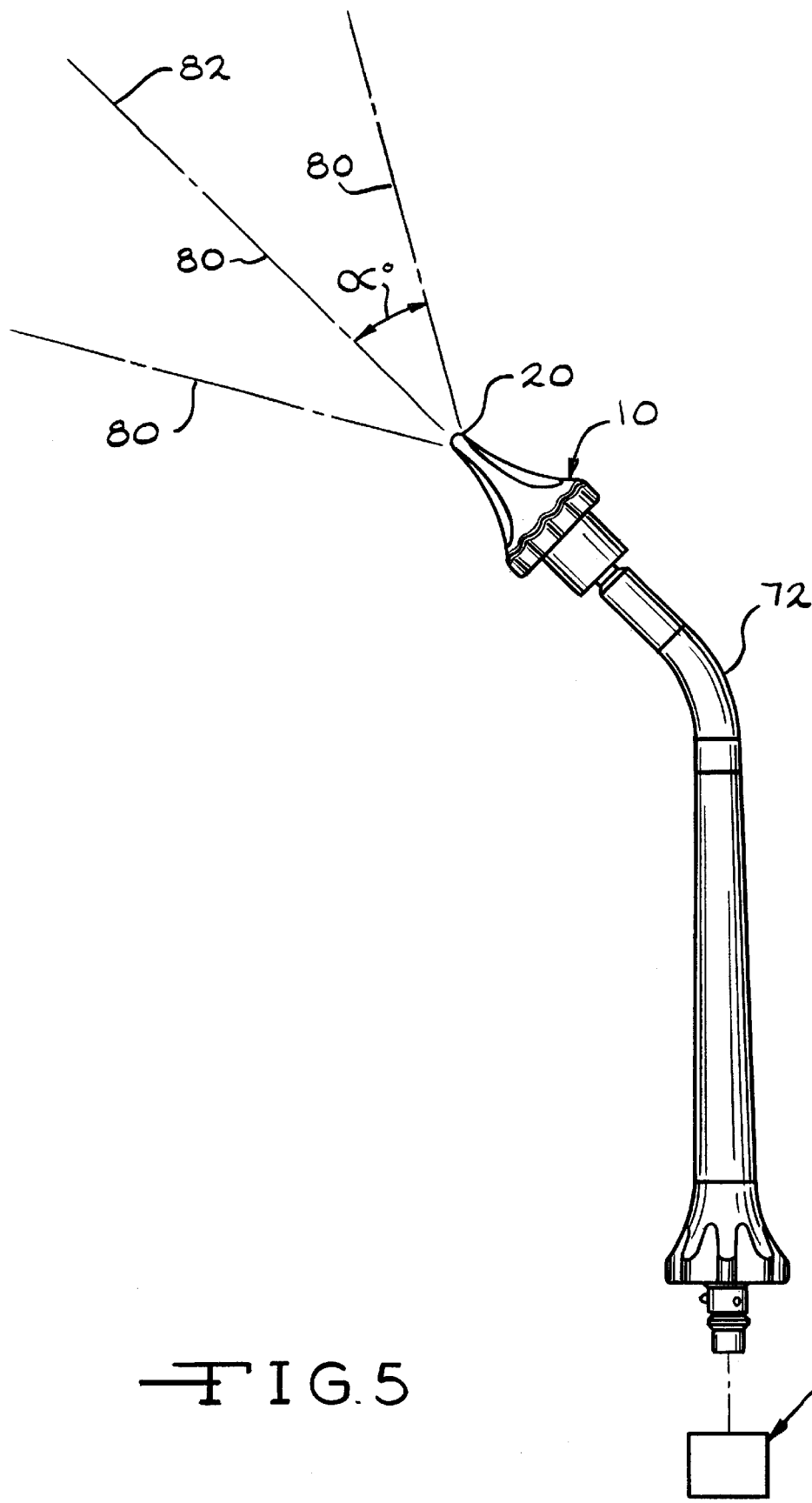
FIG. 5 is a side elevation view, partially in phantom, of an irrigation device attached to a supply of irrigating fluid.
Figure 6:
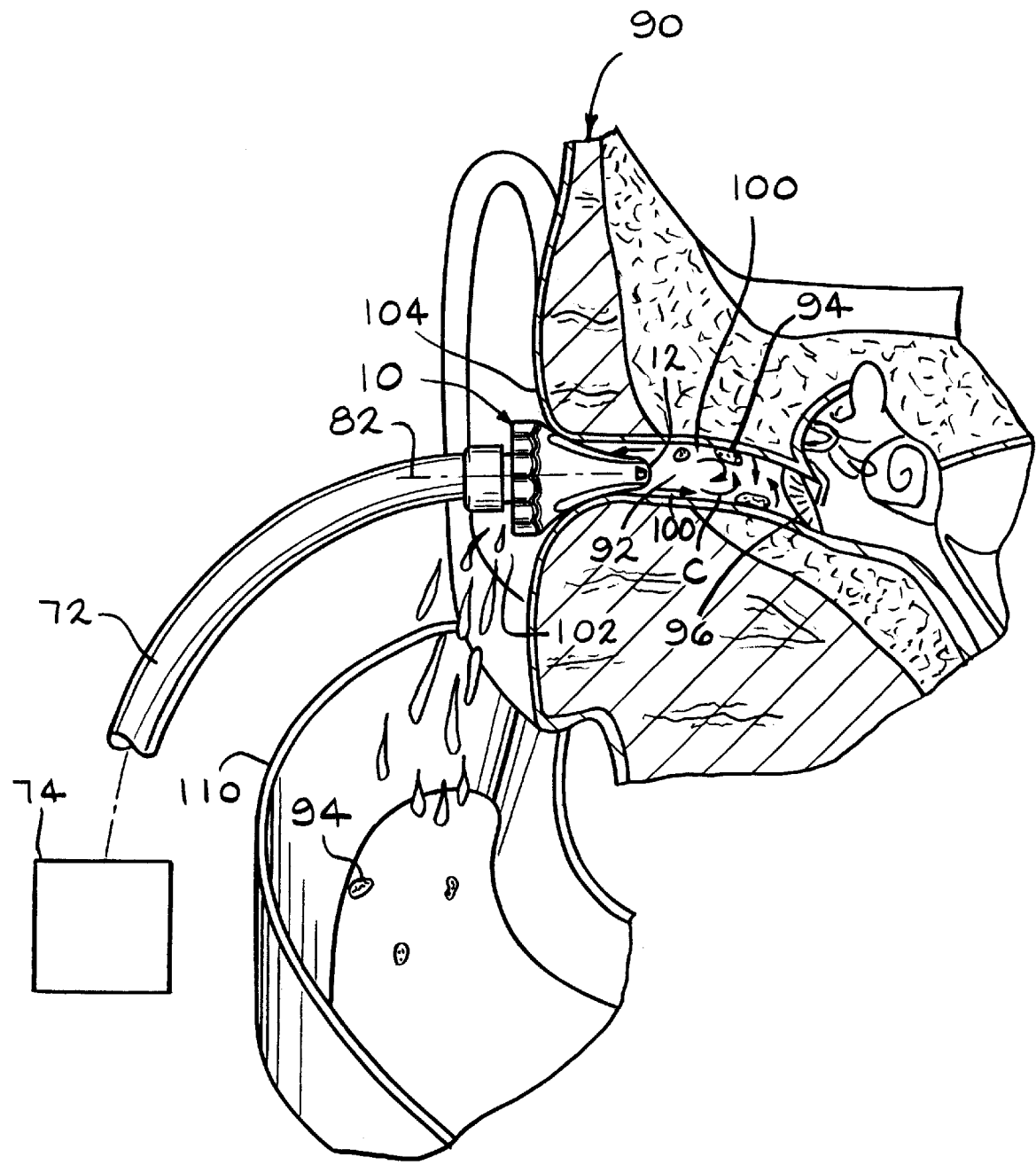
FIG. 6 is a side elevation view, partially in cross-section, of an irrigation device being used in a patient's ear.

The device 10 further comprises a flared or external fluid directional member 30 which is preferably integrally molded with the tubular member 14. The profile of the flared member 30 is generally a curve revolved around a center axis. The flared member 30 is coaxially positioned with respect to the tubular member 14. The flared member defines a tip or distal end 32 in close proximity to the distal end 12 of the tubular member 14. The flared member 30 further defines a base 34 which is in a spaced apart relationship to the tip 32. The flared member 30 flares in a generally radially outward direction toward the proximal end 13. In certain applications, the tip 32 can be adjacent the distal end 12 of the tubular member 14. It should be understood, however, that the tip 32 of the flared member 30 can begin at a point that is spaced apart from the distal end 12 of the tubular member 14. The flared member 30 terminates at the base 34. It is preferred that the circumference of the base 34 be larger than the circumference of the orifice being examined. The base 34 of the flared member 30 prevents the irrigation device 10 from being over inserted into the orifice being examined. In practice, the irrigation device 10 is typically stopped by the sides of the orifice being examined at a point between the base 34 and the tip 32 of the flared member 30. The base 34 can have a textured, scalloped or indented perimeter 36. The scalloped perimeter 36 aids the user in attaching and removing the irrigation device 10 from an adapter 72 which is connected to a source of pressurized fluid 74, as shown in FIGS. 5 and 6.

Figure 2B:
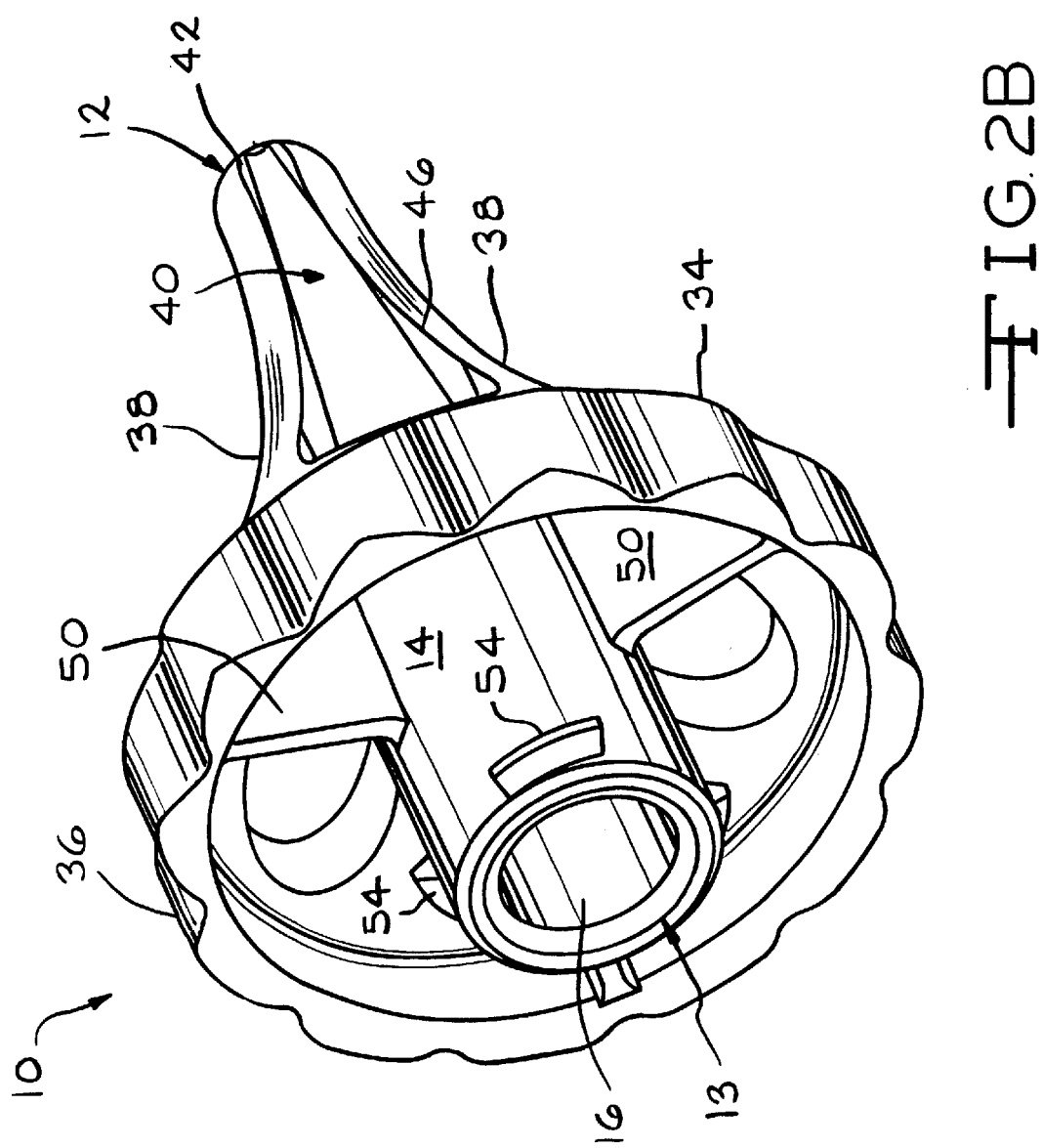
FIG. 2B is a rear perspective view of an irrigation device.
Figure 3A:
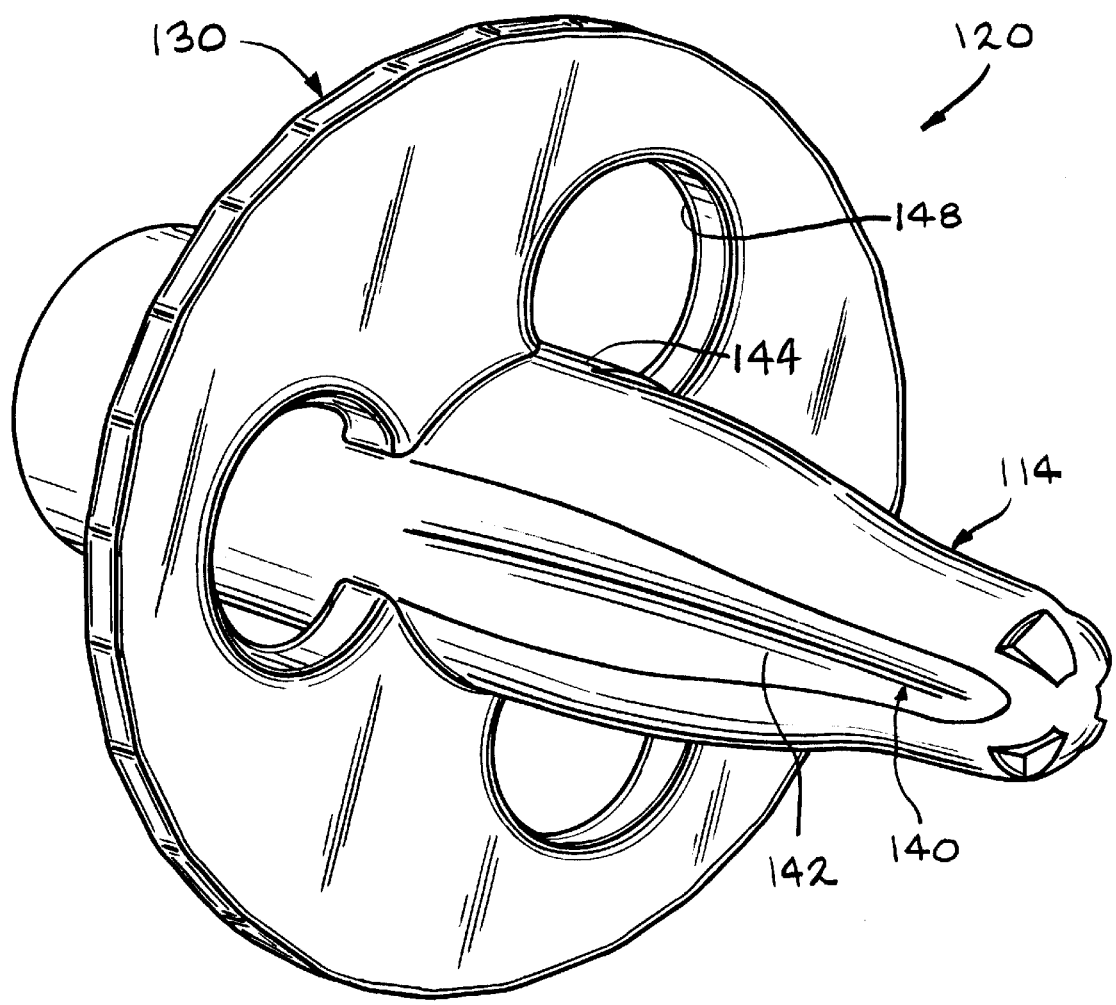
FIG. 3A is a front perspective view of another irrigation device.
Figure 3B:
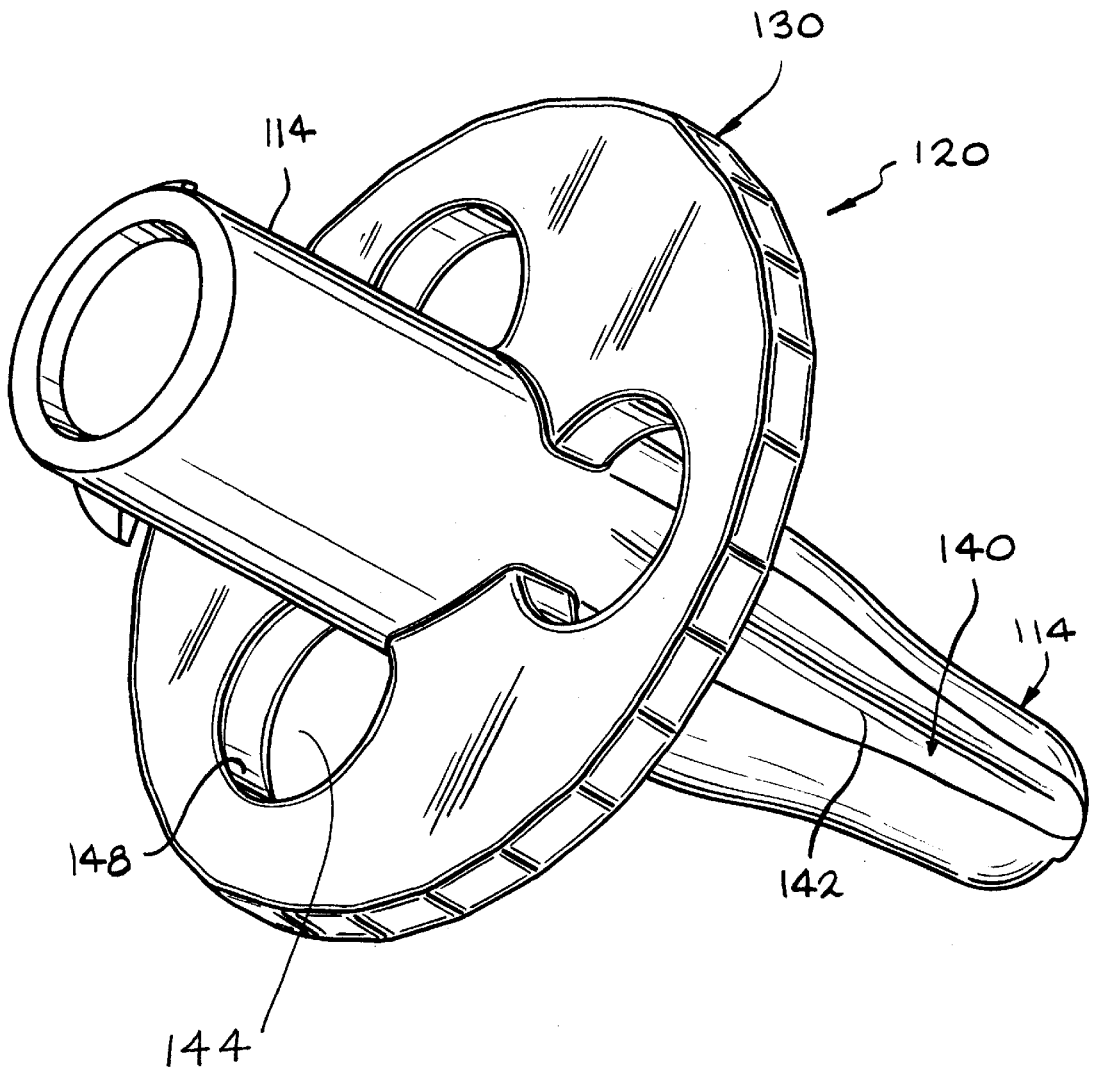
FIG. 3B is a rear perspective view of another irrigation device.

Another feature of the present invention is shown in FIGS. 3A and 3B. The device 120 shown in FIGS. 3A and 3B comprises a flange or external fluid directional member 130 which is preferably integrally molded with a tubular member 114. It should be further understood that the flared member 30 (as shown in FIGS. 1–2B) and the flange member 130 (as shown in FIGS. 3A and 3B) both prevent over insertion of the devices 10 and 120' into the orifice being examined. It is to be further understood that the flange member 130 can be positioned at various points along the longitudinal axis of the tubular member 114. The flange member 130 is spaced apart from the distal end of the tubular member 114 and extends radially from the tubular member 114. In certain embodiments it is contemplated that the flange member 130 can extend at a substantially perpendicular angle from the tubular member 114. In other embodiments, the flange member 130 can extend at an acute angle with respect to the proximal end of the tubular member 114.

Referring again to FIGS. 1–2B and 4–6, the flared member 30 defines a plurality of flared sides 38 which extend from the tip 32 to the base 34. As the flared sides 38 extend from the tip 32 to the base 34, the flared sides 38 increase nonlinearly in circumference.

The flared member 30 also defines a plurality of longitudinally extending passageways 40 along an outer surface of the tubular member 14. Each passageway 40 is usually equally spaced with radial symmetry around the central axis of the bore 16. Each passageway 40 has an adequate size to readily permit cumulated fluid to escape without build-up of excessive pressure that could damage delicate anatomy in proximity to the irrigation device 10.

The passageway 40 continuously extends from the tip 32 toward the base 34 of the flared member 30. Each passageway 40 defines an open channel 42 which is adjacent the tip 32 of the flared member 30 and an enclosed channel 44 which is adjacent the base 34 of the flared member 30. The open channel 42 is contiguous the enclosed channel 44. The enclosed channel 44 is defined by the flared side 38. The channels 42 and 44 define the exit passageway 40 for fluid by prohibiting a liquid tight seal from being created. Each of the open channels 42 begins at the distal end 12 of the tubular member 14 with a generally concave shape that transitions to a generally convex shape at the enclosed channel 44. The passageway 40 is defined by walls 46 which extend in a radially outward direction to form the flared side 38 of the flared member 30. As the passageway 40 extends toward the base 34, the passageway 40 becomes the enclosed channel 44. In the embodiment shown, each of the enclosed channels 44 has a generally convex shape and generally follows the circumferential shape of the proximal end 13 of the tubular member 14. The complex/transitioning shape of the open channel 42 and the convex shape of the enclosed channel 44 permit irrigation fluid to pass through the device 10 before excessive pressure can build-up and damage delicate anatomy. The open channels 42 generally define a greater cross-section than the cross-sections of the orifices 20 so that there is always sufficient drainage of fluid from the passageways 40.

The enclosed channel 44 defines an entrance 48 which is formed by the flared side 38 of the flared member 30. Each entrance has a predetermined geometric configuration. For example, as seen in the figures, each entrance 48 of the enclosed channel 44 generally defines an elliptical or tear drop shape. However, it is to be understood that the entrance 48 can have other geometric configurations such as round, oval and the like, and that other geometric configurations are within the contemplated scope of the present invention.

It is to be understood that the device 120, shown in FIGS. 3A and 3B, also has a plurality of passageways 140 which define open channels 142 and enclosed channels 144. Each enclosed channel 144 is defined by an opening 148 in the flange member 130. As described above, the open channels 142 have a generally concave shape that transitions to a generally convex shape at the enclosed channels 144. It is also to be understood that the openings 148 can have any desired predetermined geometric configuration, as described above.

Referring again to FIGS. 1–2B and 4–6, a plurality of support ribs 50 can be spaced along the outer circumference of the tubular member 14 with radial symmetry such that the ribs 50 extend between the tubular member 14 and the flared member 30. The ribs 50 can be integrally molded to the flared portions 38 of the flared member 30. The ribs 50, the outer circumference of the tubular member 14, the entrance 48 and the base 34 of the flared member 30 define the enclosed channel 44. The ribs 50 support and reinforce the flared member 30 and guide the exiting fluid out of the passageway 40.

In operation, a pressurized irrigation fluid enters the device 10 at the proximal end 13 of the tubular member 14 through the bore 16. A portion of the stream contacts the internal baffle 26 and is deflected out the orifices 20, as shown by arrows labeled "A" in FIG. 4. Another portion of the stream travels through the bore 16 and exits the orifice 20 without contacting the internal baffle 26, as shown by arrows labeled "B" in FIG. 4. As the streams A and B both exit the orifice 20, the streams A and B contact and intersect, causing a spray of pressurized fluid, as shown by arrows labeled "C" in FIG. 4, to form. The pressurized fluid contacts and dislodges any debris located in the environment where the irrigation device is being used. The pressurized fluid and debris exit at the tip 32 of the flared member 30 by flowing along the open channels 42 and into the enclosed channels 44. The relatively large diameter defined by the flared member 30 allows the fluid and debris to exit the device both easily and at a greatly reduced pressure.

In certain applications, the proximal end 13 of the tubular member 14 can further comprise a plurality of spaced apart locking attachment means 54 which conform to international standards such as ISO 594-2:1991(E). It should be understood that it is within the contemplated scope of the present invention that the device 10 can be attached to a source of pressurizing fluid using any suitable connecting means, including, for example an interfering tapering fit, a threaded connection or an annular shape fit. It is to be understood that other types of connecting means are within the contemplated scope of the present invention. It is further to be understood that the pressurized irrigation fluid can be supplied by generally known irrigation devices such as syringes or dental irrigation devices.

Referring now to FIG. 5, the irrigating device 10 is removably connected to a adapter 72 such as a male lure lock connector. The adapter 72 is operatively connected to a source of pressurized fluid 74, such as a conventional dental irrigation device. FIG. 5 also shows a stream 80 of pressurized irrigating fluid erupting from the orifices 20 of the irrigating device 10. The streams 80 erupt from the orifices 20 at an angle a with respect to a central axis 82 extending through the device 10. In practice, it has been determined that an angle of about between 30° and 45° is an effective angle in which to quickly remove impacted cerumen without patient discomfort or excessive messiness.

As shown in FIGS. 1, 2, 4, 5 and 6, the internal geometry of the irrigation device 10 allows the plurality of streams of water to exit the distal end 12 at an angle to the central axis 82 whereby the streams only contact the walls of the ear canal and not the tympanic membrane. The profile of the flared member 30 allows deeper insertion into the ear canal 92 and maximizes the area of the open channels 42 leading to the enclosed channels 44 of the passageway 40, thereby allowing for the escape of fluid and debris without a build-up of pressure. However, the profile of the flared member 30 also prevents the irrigation device 10 from being positioned too close to the tympanic membrane, thereby preventing even the angled streams of fluid from directly contacting the tympanic membrane.

FIG. 6 is a schematic drawing of a person's ear 90 receiving irrigation. The irrigation device 10 is partially inserted into an ear canal 92 of a person to safely remove cerumen 94 from the ear canal 92. The ear 90 comprises the ear drum 96 which is the distal terminus to the ear canal 92. The ear canal 92 is often obstructed by cerumen 94. When obstructed with cerumen 94, a physician cannot fully visualize the ear drum 96 making diagnosis of infection difficult or impossible. The irrigation device of the present invention is useful in removing this cerumen 94 through flushing by directing pressurized fluid 100, such as warm water, indirectly into the ear canal 92. The irrigation device 10, when connected to the irrigating device 74, safely delivers pressurized fluid indirectly into the ear canal 92. In operation, the irrigation device is removably connected to the fluid source 74 and then inserted into the ear canal 92. The flared member 30 of the device 10 defines a circumferential diameter larger than the opening between the tragus, antitragus 102 and the concha 104 of the ear 90, thereby prohibiting over insertion of the irrigation device 10 into the ear canal 92. The irrigation device 10 directs a plurality of streams 100 of fluid which exit the orifices 20 from the distal end 12 at an angle from the central axis 82 extending through the device 10. The direction of the fluid only permits contact of the fluid with the walls of the ear canal 92 rather than directly contacting the tympanic membrane 96. The streams of fluid generally shown by arrows "C" combine to form a turbulent lavage that loosens and then expels the cerumen 94 through the passageways 40 in the flared member 30.

Since irrigation is typically a very a messy procedure requiring several minutes to administer the pressurized fluid, the volume of the fluid administrated accumulates very quickly and must be collected in a basin. The present invention reduces the mess because the turbulent lavage created inside the ear canal when the divergent streams contract the walls of the channel provides a very effective mechanism for loosening and expelling debris and cerumen. This efficiency reduces the time required to perform the procedure, thereby reducing the volume of water or fluid to be utilized.

Another advantage of the present device 10 is that the flared member 30 acts as a funnel to capture the discharged fluid coming through the passageways 40 and directs the discharged fluid into a collection basin 110. This avoids fluid run off onto the patient which often causes discomfort. Still a further benefit is that the present device can be used by one person by holding the pressurized irrigation device in one hand while holding a catch basin in the other hand.

It will be understood by those who practice the invention and by those skilled in the art, that various modifications and improvements can be made to the invention without departing from the spirit of the disclosed concept. The scope of protection afforded is to be determined by the claims and by the breadth of interpretation allowed by law.

We claim:
1. An irrigation device comprising a tubular member having a distal end and a proximal end and at least one bore axially extending from the proximal end to the distal end, the bore terminating at a plurality of orifices which extend at an angle from the bore, and a flared member coaxially positioned with respect to the tubular member, the flared member defining a tip in close proximity to the distal end of the tubular member and a base which is in a spaced apart relationship from the tip of the flared member, the flared member defining a plurality of flared sides extending from the tip to the base, whereby as the flared sides extend from the tip to the base, the flared sides increase in circumference, the flared member defining at least one passageway, the passageway defining at least one open channel adjacent the tip of the flared member and at least one enclosed channel adjacent the base of the flared member, the enclosed channel being defined by the flared sides and the base of the flared member, wherein the bore has a first internal tapered surface having a decreasing circumference as the bore extends toward the distal end of the tubular member, the bore further including at least a second internal tapered surface having a decreasing circumference as the bore extends toward the distal end of the tubular member, whereby the first tapered surface slopes toward the distal end at an angle that is different from a slope of the second tapered surface.

2. The device of claim 1, wherein the open channels and the enclosed channels allow an exit for fluid from the flared member by prohibiting a liquid tight seal from being created during use.

3. The device according to claim 1, wherein the fluid exits the open and enclosed channels without a build-up of excessive pressure during use.

4. The device of claim 1, wherein the device is removably attached to a source of pressurized irrigating fluid using a suitable connection means.

5. An irrigation device comprising a tubular member having a distal end and a proximal end and at least one bore axially extending from the proximal end to the distal end, the bore terminating at a plurality of orifices which extend at an angle from the bore, and a flared member coaxially positioned with respect to the tubular member, the flared member defining a tip in close proximity to the distal end of the tubular member and a base which is in a spaced apart relationship from the tip of the flared member, the flared member defining a plurality of flared sides extending from the tip to the base, whereby as the flared sides extend from the tip to the base, the flared sides increase in circumference, the flared member defining at least one passageway, the passageway defining at least one open channel adjacent the tip of the flared member and at least one enclosed channel adjacent the base of the flared member, the enclosed channel being defined by the flared sides and the base of the flared member, and at least one support rib extending radially between the tubular member and the flared member to help capture and direct escaping effluent.

6. The device of claim 5, wherein a plurality of support ribs are spaced with radial symmetry around the tubular member.

7. An irrigation device comprising a tubular member having a distal end and a proximal end and at least one bore axially extending from the proximal end to the distal end, the bore terminating at a plurality of orifices which extend at an angle from the bore, and a flared member coaxially positioned with respect to the tubular member, the flared member defining a tip in close proximity to the distal end of the tubular member and a base which is in a spaced apart relationship from the tip of the flared member, the flared member defining a plurality of flared sides extending from the tip to the base, whereby as the flared sides extend from the tip to the base, the flared sides increase in circumference, the flared member defining at least one passageway, the passageway defining at least one open channel adjacent the tip of the flared member and at least one enclosed channel adjacent the base of the flared member, the enclosed channel being defined by the flared sides and the base of the flared member, wherein the tubular member directs a stream of pressurized irrigating fluid out of the orifices at an angle between about 30° and about 45° with a central axis of the device.

8. An irrigation device comprising a tubular member having a distal end and a proximal end and at least one bore axially extending from the proximal end to the distal end, the bore terminating at a plurality of orifices which extend at an angle from the bore, and a flared member coaxially positioned with respect to the tubular member, the flared member defining a tip in close proximity to the distal end of the tubular member and a base which is in a spaced apart relationship from the tip of the flared member, the flared member defining a plurality of flared sides extending from the tip to the base, whereby as the flared sides extend from the tip to the base, the flared sides increase in circumference, the flared member defining at least one passageway, the passageway defining at least one open channel adjacent the tip of the flared member and at least one enclosed channel adjacent the base of the flared member, the enclosed channel being defined by the flared sides and the base of the flared member, wherein the distal end of the tubular member further includes an internal baffle extending axially inward in the bore in a direction toward the proximal end of the tubular member.

9. The device of claim 8, wherein the internal baffle deflects the stream of oncoming pressurized irrigating fluid toward the orifices.

10. The device of claim 9, wherein at least one side wall of the internal baffle is substantially parallel to at least one side wall defining the orifice.

11. The device of claim 9, wherein the internal baffle has a predetermined geometric configuration.

12. The device of claim 11, wherein the internal baffle has a generally conical configuration.

13. The device of claim 8, wherein the internal baffle has an included angle between 60° and 120°.

14. An irrigation device comprising a tubular member having a distal end and a proximal end and at least one bore axially extending from the proximal end to the distal end, the bore terminating at the distal end at a plurality of orifices which extend at an angle from the bore, the distal end of the tubular member defining an internal baffle extending axially inward in the bore in a direction toward the proximal end of the tubular member, and a flared member coaxially positioned with respect to the tubular member, the flared member defining a tip in close proximity to the distal end of the tubular member and a base which is in a spaced apart relationship from the tip of the flared member, the flared member defining a plurality of flared sides extending from the tip to the base; whereby as the flared sides extend from the tip to the base, the flared sides increase in circumference, the flared member defining at least one passageway, the passageway defining at least one open channel adjacent the tip of the flared member and at least one enclosed channel adjacent the base of the flared member, the enclosed channel being defined by the flared sides and the base of the flared member.

15. The device of claim 14, wherein the open channel begins at the distal end of the tubular member with a concave cross-section and transitions to a convex cross-section at an entrance of the enclosed channel and wherein the enclosed channel has a convex cross-section.

16. The device of claim 14, further including at least one support rib extending radially between the tubular member and the flared member to help capture and direct escaping effluent.

17. The device of claim 14, wherein the internal baffle deflects the stream of oncoming pressurized irrigating fluid toward the orifices at an angle between about 30° and about 45° with a central axis of the device.

18. The device of claim 14, wherein at least one side wall of the internal baffle is substantially parallel to at least one side wall defining the orifice.

19. The device of claim 14, wherein the internal baffle has a predetermined geometric configuration.

20. The device of claim 19, wherein the internal baffle has a generally conical configuration.

21. The device of claim 14, wherein the internal baffle has an included angle between 60° and 120°.

22. An irrigation device comprising a tubular member having a distal end and a proximal end and at least one bore axially extending from the proximal end to the distal end, the bore terminating at the distal end at a plurality of orifices which extend at an angle from the bore, the distal end of the tubular member defining an internal baffle extending axially inward in the bore in a direction toward the proximal end of the tubular member.

23. The device of claim 22, wherein the internal baffle deflects the stream of oncoming pressurized irrigating fluid toward the orifices.

24. The device of claim 23, wherein at least one side wall of the internal baffle is substantially parallel to at least one side wall defining the orifice.

25. The device of claim 22, wherein the internal baffle has a predetermined geometric configuration.

26. The device of claim 22, wherein the internal baffle has a generally conical configuration.

27. The device of claim 22, wherein the internal baffle has an included angle between 60° and 120°.

28. The device of claim 22, wherein the tubular member directs a stream of pressurized irrigating fluid out of the orifices at an angle between about 30° and about 45° with a central axis of the device.

29. The device of claim 22, wherein the distal end of the tubular member has between 2 and 10 orifices.

30. The device of claim 22, wherein each orifice terminates at a recessed cavity that extends through the distal end of the tubular member.

* * * * *